(12) United States Patent
Bruder et al.

(10) Patent No.: US 8,396,275 B2
(45) Date of Patent: Mar. 12, 2013

(54) X-RAY CT SYSTEM AND METHOD FOR CREATING TOMOGRAPHIC RECORDINGS WITH TWO X-RAY ENERGY SPECTRA

(75) Inventors: Herbert Bruder, Höchstadt (DE); Thomas Flohr, Uehlfeld (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 825 days.

(21) Appl. No.: 12/588,248

(22) Filed: Oct. 8, 2009

(65) Prior Publication Data

US 2010/0092060 A1 Apr. 15, 2010

(30) Foreign Application Priority Data

Oct. 9, 2008 (DE) .......................... 10 2008 051 043

(51) Int. Cl.
*A61B 6/03* (2006.01)
(52) U.S. Cl. ..................... 382/131; 378/5; 378/8; 378/9
(58) Field of Classification Search .................. 378/5, 8, 378/9; 382/131
See application file for complete search history.

(56) References Cited

U.S. PATENT DOCUMENTS

| | | |
|---|---|---|
| 2007/0041490 A1 | 2/2007 | Jha |
| 2008/0144765 A1 | 6/2008 | Flohr |
| 2009/0135994 A1* | 5/2009 | Yu et al. ............................ 378/5 |
| 2009/0161935 A1 | 6/2009 | Bruder et al. |

FOREIGN PATENT DOCUMENTS

| | | |
|---|---|---|
| DE | 102006056884 A1 | 6/2008 |
| DE | 102007061935 A1 | 6/2009 |

OTHER PUBLICATIONS

Schmidt et al., Comparison of Temporal Resolution in Dual-Source (DS) Images and Dual-Energy Images Based on Cardiac Motion Phantom, Dec. 1, 2009, RSNA 2009, Abstract code: SSG18-04.*

* cited by examiner

*Primary Examiner* — Toan Ton
*Assistant Examiner* — John Corbett
(74) *Attorney, Agent, or Firm* — Harness, Dickey & Pierce, P.L.C.

(57) ABSTRACT

An x-ray CT system and a method are disclosed for creating tomographic recordings with the aid of an x-ray CT system, with two emitter/detector arrangements operating with an angular offset on a gantry with at least two different x-ray energy spectra. In at least one embodiment, at least one first recording is reconstructed from detector data from two quarter rotations with different x-ray energy spectra and at least one second recording is created from detector data of a scan of at least one of the emitter/detector arrangements over a half rotation. According to at least one embodiment of the invention, the recordings are subjected to high-pass filtering or low-pass filtering in respect of their spatial frequencies and then the filtered recordings are combined to give a resulting recording.

32 Claims, 5 Drawing Sheets

X-RAY CT SYSTEM AND METHOD FOR CREATING TOMOGRAPHIC RECORDINGS WITH TWO X-RAY ENERGY SPECTRA

PRIORITY STATEMENT

The present application hereby claims priority under 35 U.S.C. §119 on German patent application number DE 10 2008 051 043.2 filed Oct. 9, 2008, the entire contents of which are hereby incorporated herein by reference.

FIELD

At least one embodiment of the invention generally relates to an x-ray CT system and/or a method for creating tomographic recordings with the aid of an x-ray CT system with two emitter/detector arrangements operating with an angular offset on a gantry with at least two different x-ray energy spectra, with at least one recording being created from detector data of a scan of at least one of the emitter/detector arrangements over a half rotation.

BACKGROUND

X-ray CT systems and methods for creating tomographic recordings are generally known. In particular methods are known, with which the temporal resolution is doubled with the aid of two emitter/detector arrangements offset at an angle on a gantry compared with CT systems with one emitter/detector arrangement. However here both emitter/detector arrangements are operated with the same x-ray energy spectrum, so that the information obtained by way of the emitter/detector arrangements is consistent per se. If simultaneous scanning takes place with different x-ray energy spectra, the resulting projections can in principle be reconstructed into one image with high temporal resolution. However the different x-ray energy spectra used to obtain the projections result in images with disruptive artifacts.

In practice there is on the one hand a desire to obtain more information about the composition of the examination object by using different x-ray spectra when scanning with a two-emitter/detector arrangement than is possible when scanning with a single spectrum. At the same time a high level of temporal resolution is desirable, particularly during a cardiac examination, in which process the combination of these two requirements should not result in an increased dose burden.

SUMMARY

At least one embodiment of the invention is directed to an x-ray CT system and/or a method for creating tomographic recordings, which on the one hand is to allow CT recordings with a high level of temporal resolution and on the other hand is to allow displays with a high level of material differentiation. Finally both requirements are to be satisfied without an additional dose burden.

In cardiac CT in particular the primary objective is to achieve the highest possible level of temporal resolution. With Dual Source CT (DSCT) this is achieved in that the data segment of projection data over 180° projection angles required as a minimum for reconstruction purposes is composed respectively from a 90° data segment from two emitter/detector arrangements on the gantry of the DSCT system. This gives a temporal resolution, which corresponds to a quarter of the rotation time for a 360° turn. If both emitter/detector arrangements are operated at a different voltage, in other words the CT system is operated as Dual Energy CT (DECT), each of the emitter/detector arrangements per se behaves as a conventional single-tube CT with a single emitter/detector arrangement. The temporal resolution for mono-segment reconstructions is therefore limited to half of a full rotation time.

Multi-segment reconstructions would theoretically impact in the same manner on DSCT and DECT cardiac scans. However there is no change to the factor two between temporal resolutions. A further scan would therefore have to be taken at the same voltage on both systems, which would mean double radiation exposure and the further disadvantage of an increased quantity of contrast agent.

When considering reconstructions from combined dual energy scans the inventors noticed however that the artifacts occur essentially in the low-frequency spatial frequency range, while the high-frequency image components, such as edge information, are barely disrupted. The inventors have now identified that it is possible to extract the "useful" temporally high-resolution information from a combined image with high temporal resolution consisting of two 90° data segments that complement one another to 180°, recorded with different x-ray energy spectra, by corresponding high-pass filtering and to combine this with the low-frequency information from an image to produce a resulting image. The low-frequency image components here can originate from one image recorded with just one x-ray energy spectrum or they can originate from two images, in each instance images generated with one x-ray energy spectrum, with the image information only being combined to produce the final image.

However two images can also particularly advantageously be produced initially with different x-ray energy spectra in each instance and then be combined in a manner known per se with noise optimization. The low-frequency components are then extracted from the noise-optimized combination image with low temporal resolution by low-pass filtering and combined with the high-frequency parts of the image with high temporal resolution from two different x-ray energy spectra to produce a final image.

The resulting images thus obtained on the one hand have high temporal resolution and utilize the entire applied dose. On the other hand it is also possible to analyze the two reconstruction images from just one x-ray spectrum respectively with the data records obtained from the scans to obtain detailed information about the composition of the examination object, for example using known material decomposition methods. The applied dose therefore remains the same as for a dual energy scan but enables a temporal resolution which would only be possible in known circumstances with a dual source scan and would therefore result in an additional dose burden.

Based on this knowledge the inventors propose a method, in at least one embodiment, for creating tomographic recordings with the aid of an x-ray CT system, which uses two emitter/detector arrangements operating with an angular offset on a gantry to scan an examination object simultaneously with at least two different x-ray energy spectra in a spiral or circular manner, comprising:

a first recording being reconstructed from combined detector data of a scan of a first emitter/detector arrangement over a quarter rotation (=scan over 90°+fan angle ½) with a first x-ray spectrum and detector data of a scan of a second emitter/detector arrangement over a complementary quarter rotation (=scan over 90°+fan angle ½) with a second x-ray spectrum, at least one second recording being created from detector data of a scan of at least one of the emitter/detector arrangements over a half rotation (=scan over 180°+fan angle), the first recording being subjected to high-pass filtering in respect of its spatial frequencies and the at least one second recording being subjected to low-pass filtering in respect of its spatial frequencies and the filtered recordings being combined to produce a resulting recording.

This resulting recording can now be stored in a storage unit and/or displayed and/or supplied for further processing.

This method described above creates a resulting recording from the scan data of a dual energy scan, the resulting recording having a temporal resolution similar to the recording of a dual source scan without an additional radiation dose having to be applied.

Just one second recording can advantageously be created from a noise-optimized combination of two reconstructed recordings from detector data of one x-ray spectrum respectively. A particularly low-noise resulting recording is created in this manner but the additional information obtained by the two x-ray energy spectra is lost.

Alternatively just one second recording can also be created from the detector data of one x-ray spectrum. If this procedure is implemented separately for both x-ray energy spectra, the additional information obtained by the two x-ray energy spectra is retained for each resulting image, with simultaneous noise reduction.

In principle it appears favorable for the high-pass and low-pass filtering to use filters $F_1$ and $F_2$, which are complementary in total so that the following applies: $F_1+F_2=1$. It is also favorable if the filters used for high-pass and low-pass filtering are isotropic, so that the most directionally neutral filtering possible results.

To filter the recordings in respect of spatial frequencies, it is possible to use a transformation, for example a Fourier transformation or wavelet transformation, of the recordings in the spatial frequency space, in which filtering can be undertaken by modifying frequency-specific coefficients. After filtering in the spatial frequency space it is then possible to back transform the filtered transformed recordings.

As an alternative for filtering the recordings in respect of spatial frequencies it is also possible to apply spatial frequency filters to the image data directly.

Filtering can also take place directly during the reconstruction of the recordings by modifying a convolution kernel.

Instead of using 180° data segments for the second recording, data segments >180°, in particular 360°, are also possible. This has the advantage of further reducing quickscan artifacts.

The inventive method of at least one embodiment can also be extended to include the use of more than two frequency bands. It would be possible to use for example a first recording—reconstructed from two 90° scans of different energy—, a second recording—combined with noise optimization from two recordings reconstructed respectively from data segments over a half rotation with different energy in each instance—and a third recording—combined with noise optimization from two scans with different energy spectra over a full rotation—as three input images $I_1$, $I_2$ and $I_3$.

At least one embodiment of the method described above is suitable in particular for creating cardiac recordings of a patient with a beating heart, for which the detector data should preferably originate from the temporal range of a cardiac cycle. It is also favorable here if the detector data originates from the temporal range of the rest phase of a cardiac cycle.

In respect of the temporal relative positioning of the detector data used it is also proposed that the temporal focus of the detector data of the first recording should be identical to the temporal focus of the detector data of the at least one second recording.

If it is anticipated that the transition from motion phase to rest phase and back to motion phase of the heart will not take place symmetrically in the pattern over time, the temporal focus of the detector data of the first recording can also be displaced in relation to the temporal focus of the detector data of the at least one second recording such that the data of the first recording is optimized in respect of its motion blur and moved into the temporal range of the detector data of the at least one second recording.

Also included in the scope of at least one embodiment of the invention with the method described above is an x-ray CT system with two emitter/detector arrangements and a control and computation unit with a program storage unit, with computer program code stored in the program storage unit and executing the method steps of at least one embodiment of the method described above during operation of the system.

BRIEF DESCRIPTION OF THE DRAWINGS

Embodiments of the invention are described in more detail below with reference to the figures, in which only the features necessary for an understanding of the invention are shown. The following reference characters and abbreviations are used: C1: CT system; C2: first x-ray tube; C3: first detector; C4: second x-ray tube; C5: second detector; C6: gantry housing; C7: patient; C8: patient support; C9: system axis; C10: computation and control unit; C11: contrast agent applicator; C12: ECG line; C13: control line; A: first emitter/detector arrangement; B: second emitter/detector arrangement; $F_k$, $F_1$, $F_2$, $F_3$: filter; $\hat{F}_1$, $\hat{F}_2$: filter functions; $Prg_1$-$Prg_n$: computer programs; $w_A$, $w_B$: weighting functions; $I_k$: input images where k=1, 2, 3; $I_A$, $I_B$: reconstructed images from 180° scans; $I_F$: resulting image; $\rho$: spatial frequency.

In the drawing.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

To simplify the representation of embodiments of the invention the procedure is described with reference to an axial layer. Embodiments of the inventive method can however also be applied to volume data.

Figure 1:
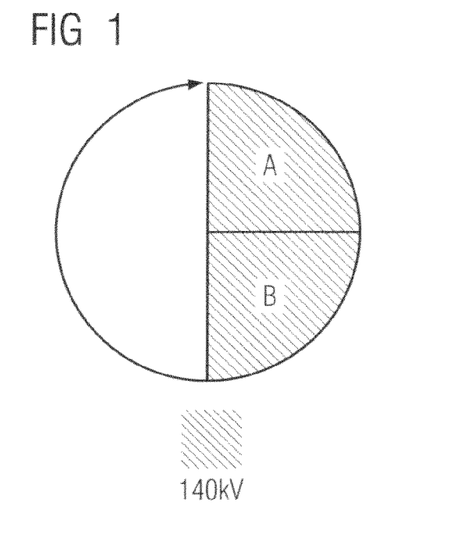
FIG. 1 shows a schematic diagram of the data segments used in a dual source CT reconstruction over 2×90°.

FIG. 1 shows a schematic diagram of the reconstruction of an image using 90° from a first emitter/detector arrangement A and 90° from a second emitter/detector arrangement B of a conventional cardiac reconstruction with identical tube voltage, both systems being arranged on a gantry with a 90° angular offset. As a result this image has a temporal resolution of a quarter of the rotation time of the gantry.

Figure 2:
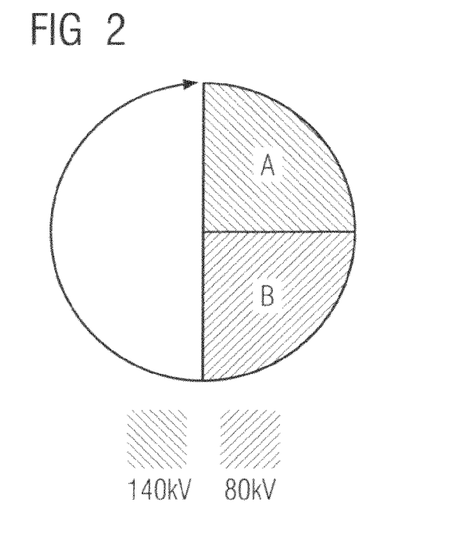
FIG. 2 shows a schematic diagram of the data segments used in a dual energy CT reconstruction over 2×90°.
Figure 3:
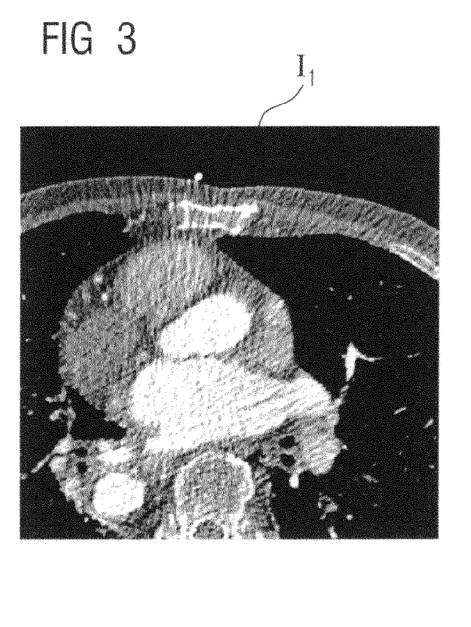
FIG. 3 shows a CT recording of a reconstruction from 2×90° CT data segments recorded respectively with different x-ray energy spectra.
Figure 4:
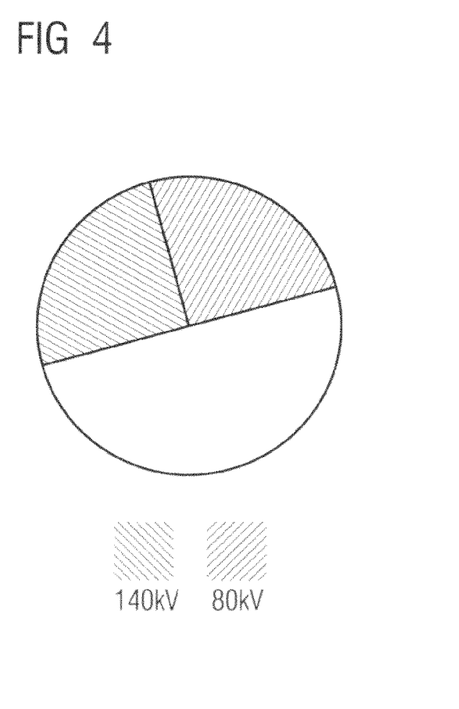
FIG. 4 shows a schematic locational diagram of the data segments used for the CT recordings from FIG. 3.

However if these two emitter/detector arrangements A and B are operated with different x-ray energy spectra, the situation shown schematically in FIG. 2 results. Since the contrast information present in the raw data of the two systems A and B is different in the different spectra, a sinogram compiled from these is inconsistent, resulting in image artifacts. Such an image $I_1$ is shown by way of example in FIG. 3. The location of the data segments with energy spectra of 140 kV and 80 kV acceleration voltage on which this image is based is shown in FIG. 4.

Since the iodine contrast in particular is highly dependent on the x-ray spectrum used, it can be seen quite clearly that the image $I_1$ becomes lighter in the direction of the 80 kV projections and darker in the direction of the 140 kV projections. The alignment of these artifacts here is a function of the start angle of the scan. In the context of cardiac CT recordings this correlation is variable with the ECG.

The inventors have however identified that the artifacts occur in the low spatial frequency range, while the high spatial frequencies, in other words the edges, are displayed satisfactorily.

Figure 5:
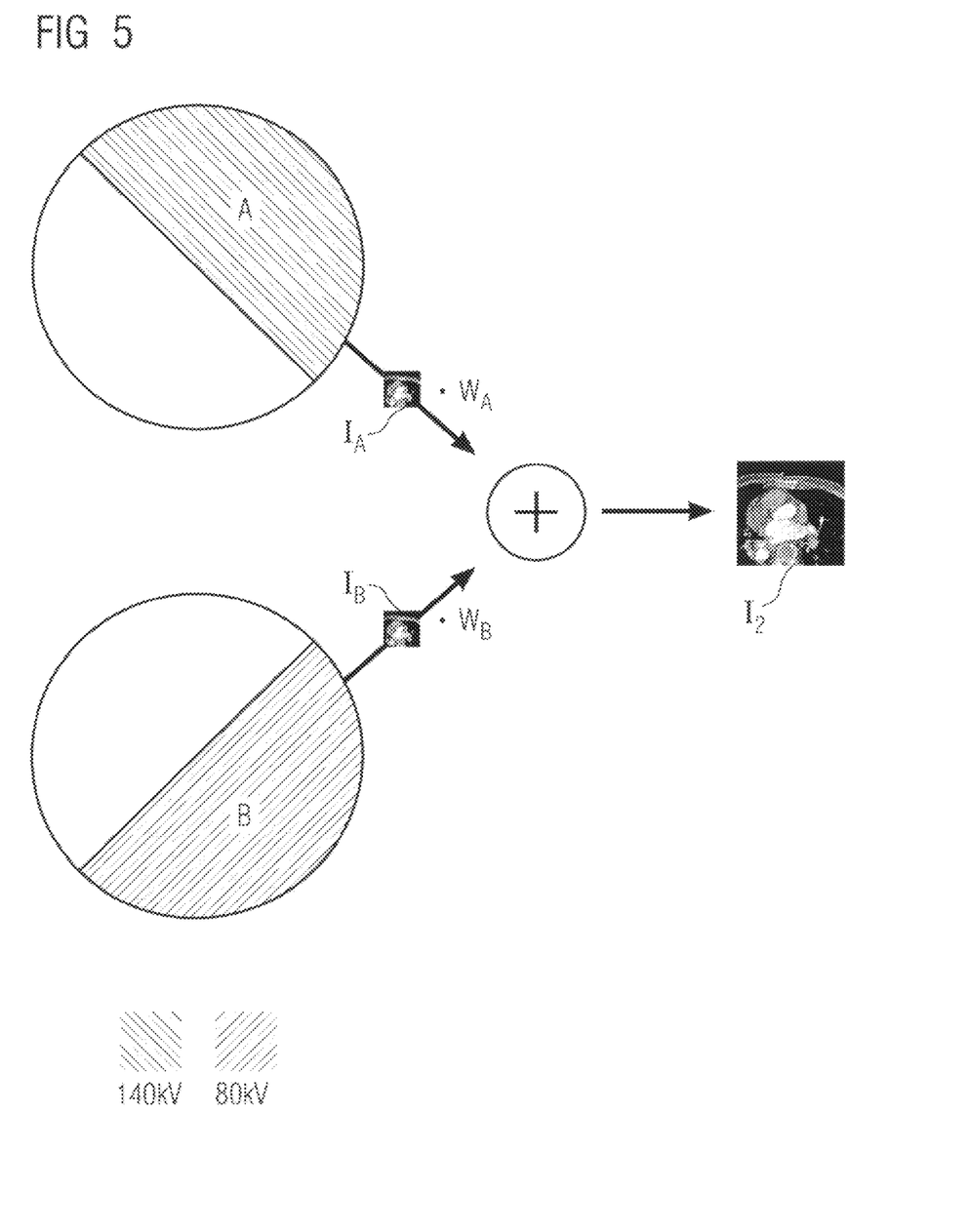
FIG. 5 shows a schematic diagram of the data segments used in the reconstruction of a dual energy CT combined image over 2×180°.

FIG. 5 also shows a schematic diagram of the reconstruction of a standard dual energy cardiac image $I_2$, in which the temporal resolution corresponds to half the rotation time, with an identical temporal focus to the one in image $I_1$ being used. This is done as usual by the separate reconstruction of two images $I_A$ and $I_B$ from 180° data segments in each instance, recorded using the emitter/detector arrangements A and B, with the two x-ray energy spectra, in this instance 80 kV and 140 kV, and subsequent weighted combining of the two images $I_A$ and $I_B$ to give the new image $I_2$. The images here can advantageously be combined by means of noise-dependent weightings, for example using the weighting factors $w_A$ and $w_B$, to obtain a noise-optimized result. Such an image now has no artifacts due to inconsistent raw data but it has a poorer temporal resolution.

Figure 6:
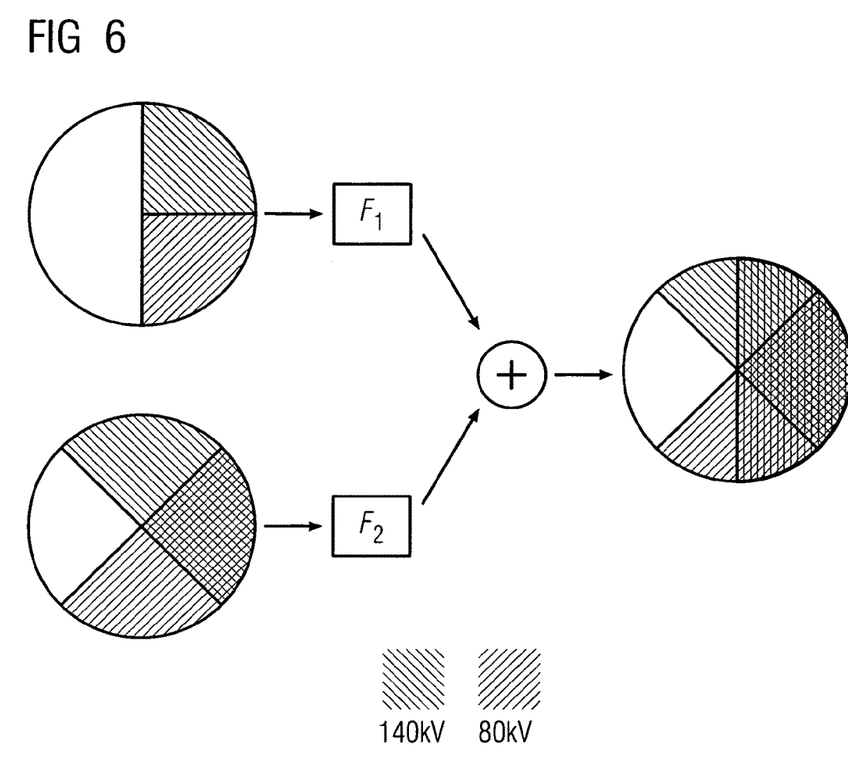
FIG. 6 shows a schematic diagram of the inventive method using a dual energy CT reconstruction with 2×90° data segments and a combined recording from two dual energy CT reconstructions respectively over 180°.

The inventors now propose calculating a new final resulting image $I_F$, with the initial images $I_k$ being filtered with, preferably isotropic, filters $F_k$ such that the high spatial frequencies are extracted from the image $I_1$ and the low spatial frequencies are extracted from the image $I_2$. The principle for this is shown in FIG. 6.

Figure 7:
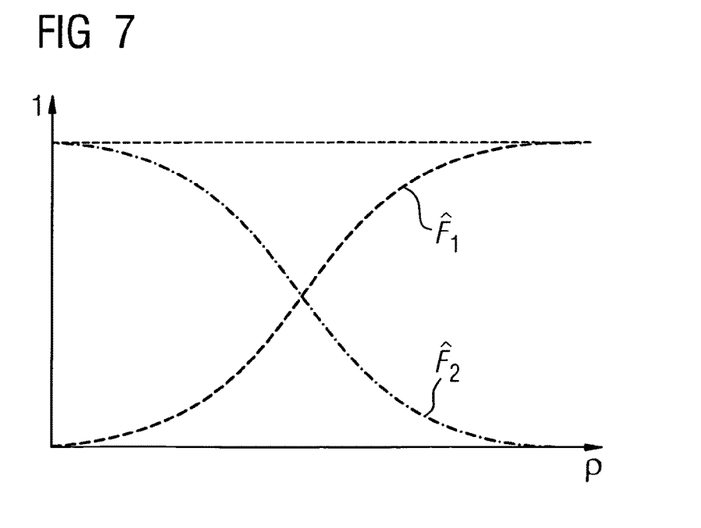
FIG. 7 shows a frequency diagram of the radial sections of two complementary spatial frequency filters used.

The filter $F_1$ and $F_2$ should expediently be complementary in the sense that $F_1+F_2\equiv 1$. This is shown in FIG. 7, where the frequency diagram of the radial sections of the filter functions $\hat{F}_1$ and $\hat{F}_2$ of the filters $F_1$ and $F_2$ is shown. The numerical values of the filter functions from 0 to 1 are shown on the ordinate here and the spatial frequency $\rho$ on the abscissa.

The final resulting image $I_F$ is then obtained by adding the filtered components, with $$I_F = F_1 * I_1 + F_2 * I_2, \quad (1)$$

where "*" describes a convolution. As a result $I_F$ has a spatial frequency-dependent time sensitivity profile, with the low-frequency background having a temporal resolution, which corresponds to half the rotation time, and high-frequency details being shown with a temporal resolution, which corresponds to a quarter the rotation time. The artifacts visible in $I_1$ are therefore eliminated while at the same time maintaining the maximum temporal sharpness of the details.

Figure 8:
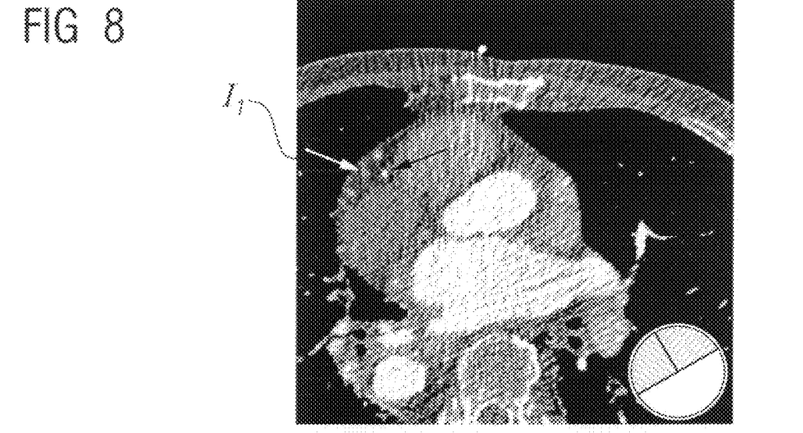
FIG. 8 shows a CT recording from two 90° data segments of a dual energy scan with two different x-ray energy spectra.

The effect of the method was examined using the example of a dual energy cardiac scan with 80 kV and 140 kV acceleration voltage. Corresponding recordings are shown in FIGS. 8 to 11. FIG. 8 shows a first recording in the form of a CT image $I_1$, which resulted from a reconstruction of raw data from two 90° scans with 80 kV—and 140 kV—spectra. It shows low-frequency artifacts, as explained above, but has the maximum possible temporal resolution.

Figure 9:
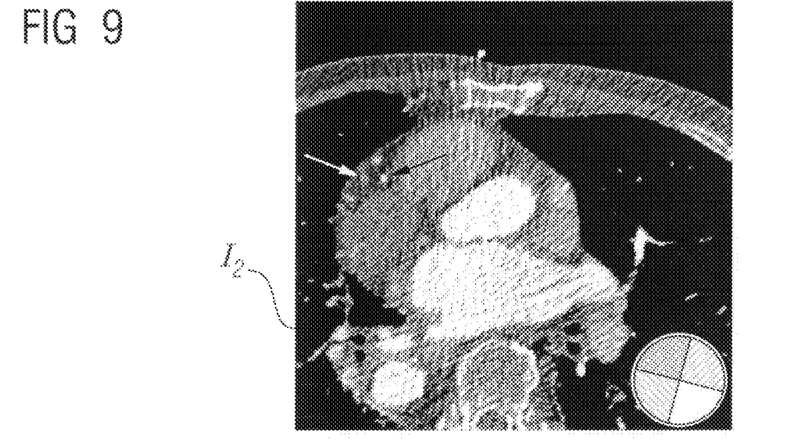
FIG. 9 shows a CT recording with noise optimization combined from two recordings from 180° data segments respectively of a dual energy scan with two different x-ray energy spectra.
Figure 10:
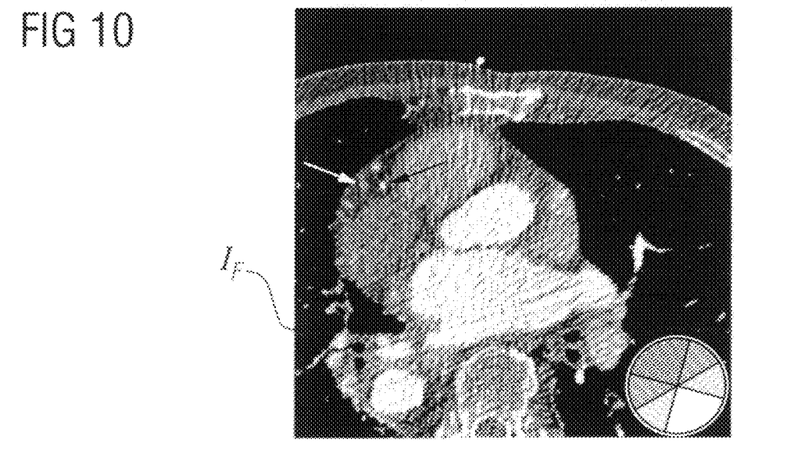
FIG. 10 shows a resulting recording as a combination of the spatial frequency filtered recordings from FIGS. 8 and 9 according to an embodiment of the inventive method and FIG. 11 shows an x-ray CT system for generating dual energy scans.

FIG. 9 shows the image $I_2$, which is a noise-optimized combination of two reconstructions respectively from 180° data segments with 80 kV and 140 kV spectra. In this image $I_2$ said artifacts disappear but the temporal resolution deteriorates by the factor two. This can be seen in particular with vessels, as shown for example with the arrows. The resulting image $I_F$ is shown in FIG. 10. It has both the high temporal resolution—in other words sharp vessels—of $I_1$ and the homogenous soft part display of image $I_2$.

The following extensions/modifications of the demonstrated method are possible:

Filtering can advantageously be undertaken directly during the reconstruction of the images $I_1$ and $I_2$. The image $I_k$ is then reconstructed with the convolution kernel $\kappa \cdot \hat{F}_k$, if $\kappa$ is the selected convolution kernel and $\hat{F}_k$ is the frequency representation of the radial section of the filter $F_k$.

Instead of using 180° data segments for $I_2$ segments >180°, in particular 360°, are also possible. This has the advantage of further reducing quickscan artifacts.

It is also possible to use more than two frequency bands, e.g. three. It would then be possible to use two 90° (A)+90° (B) scans reconstructed together to give $I_1$, two dual energy scans reconstructed separately over 180° respectively and noise optimized and then combined to give $I_2$ and two dual energy scans over 360° respectively, likewise reconstructed separately and noise-optimized and then combined to give $I_3$, as input images $I_1$, $I_2$ and $I_3$. The filters $F_k$ should then advantageously satisfy the condition $F_1+F_2+F_3\equiv 1$.

Figure 11:
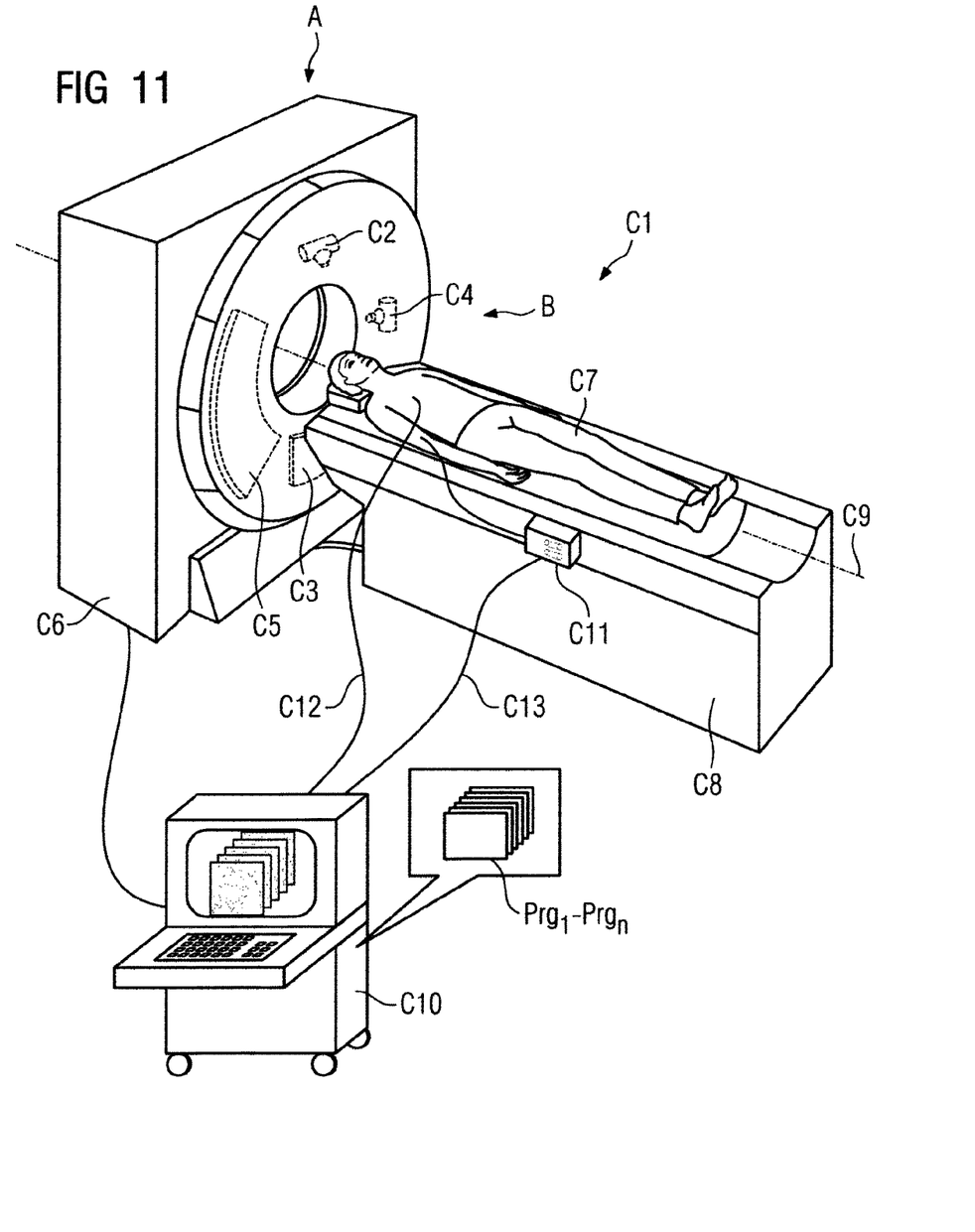

An embodiment of the invention also includes an x-ray CT system, as shown in FIG. 11. This FIG. 11 shows an exemplary dual energy CT system C1, which can be used to implement an embodiment of the inventive method. The dual energy CT system C1 has a gantry housing C6, in which a gantry (not shown in detail) is located, to which a first emitter/detector arrangement A in the form of an x-ray tube C2 with an opposite first detector C3 is secured for the scan with a first x-ray energy spectrum. A second emitter/detector arrangement B with a second x-ray tube C4 with an opposite second detector system C5 is also arranged on the gantry and can be used to perform a scan with a different x-ray energy spectrum. This CT thus allows simultaneous scanning with the two emitter/detector arrangements arranged with a 90° angular offset with two different x-ray energy spectra.

A patient C7 is present on a patient support C8 that can be displaced in the direction of the system axis C9, said patient support C8 being able to displace the patient C7 continuously or sequentially along the system axis C9 through a measuring field between the x-ray tubes and the respectively associated detectors during scanning. If the detector has sufficient width for an intended examination field, it is also possible to displace the patient with said examination field, for example the heart region, into the measuring range of the detector and carry out circular scans there in a stationary manner, in other words without further displacement. This type of scan, which has no sequential or continuous feed system, can be used particularly advantageously in the context of the inventive method for perfusion measurements. It is possible to use a contrast agent applicator C11, which is connected by way of a control line C13 to the control and computation unit C10, to administer contrast agent to the patient before or during the scanning process. By observing this contrast agent in the region of the heart it is possible to observe the perfusion of the contrast agent in the known manner and medically relevant perfusion parameters can be determined in a manner known per se.

The scanning processes are controlled by a computation and control unit C10 with the aid of computer programs $Prg_1$ to $Prg_n$. Additionally cardiac potentials of the patient C7 can be recorded with the aid of an ECG line C12 during the scanning process, so that temporally correlated information between the recorded CT data records and the heart motion can be stored. Reconstruction can also take place in the computation and control unit C10.

According to an embodiment of the invention the storage unit not only contains the programs known per se for operating the CT and for reconstructing and evaluating the scan results but also computer programs $Prg_1$ to $Prg_n$, in which an embodiment of the method described above can be implemented with the aid of the CT system illustrated here.

To summarize an embodiment of an x-ray CT system and an embodiment of a method for creating tomographic recordings with the aid of said x-ray CT system are proposed here, with two emitter/detector arrangements operating with an angular offset on a gantry being provided, which generate at least two different x-ray energy spectra, with at least one first recording being reconstructed from detector data from two quarter rotations with different x-ray energy spectra and at least one second recording being created from detector data of a scan of at least one of the emitter/detector arrangements over a half rotation. According to an embodiment of the invention the recordings are subjected to high-pass filtering or low-pass filtering in respect of their spatial frequencies and then the filtered recordings are combined to give a resulting recording.

It is obvious that the above-mentioned features of the invention can be used not only in the respectively cited combination but also in other combinations or alone, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for creating tomographic recordings with the aid of an x-ray CT systems, which uses two emitter/detector arrangements operating with an angular offset on a gantry to scan an examination object simultaneously with at least two different x-ray energy spectra in a spiral or circular manner, the method comprising:
reconstructing a first recording from combined detector data of a scan of a first of the two emitter/detector arrangements over a quarter rotation with a first x-ray energy spectrum and detector data of a scan of a second of the two emitter/detector arrangement over a complementary quarter rotation with a second x-ray energy spectrum;
creating at least one second recording from detector data of a scan of at least one of the two emitter/detector arrangements over at least a half rotation;
subjecting the first recording to high-pass filtering in respect of its spatial frequencies and subjecting the at least one second recording to low-pass filtering in respect of its spatial frequencies; and
combining the filtered first and at least one second recording to produce a resulting recording.

2. The method as claimed in claim 1, wherein only one second recording is created from a noise-optimized combination of two reconstructed recordings from detector data of one x-ray spectrum respectively.

3. The method as claimed in claim 1, wherein only one second recording is created from the detector data of one x-ray spectrum.

4. The method as claimed in claim 1, wherein only two second recordings are created from the detector data of one x-ray spectrum respectively.

5. The method as claimed in claim 1, wherein the filters used for high-pass and low-pass filtering are complementary in total.

6. The method as claimed in claim 1, wherein the filters used for high-pass and low-pass filtering are isotropic.

7. The method as claimed in claim 1, wherein, to filter the recordings in respect of spatial frequencies, a transformation of the recordings takes place in the spatial frequency space, in which filtering is undertaken by modifying frequency-specific coefficients.

8. The method as claimed in claim 7, wherein, after filtering in the spatial frequency space, a back transformation of the filtered transformed recordings is carried out.

9. The method as claimed in claim 1, wherein the filtering of the recordings in respect of spatial frequencies takes place by direct application of a spatial frequency filter to the image data.

10. The method as claimed in claim 1, wherein filtering takes place during the reconstruction of the recordings by modifying a convolution kernel.

11. The method as claimed in claim 1, wherein the at least one second recording is created from detector data of a scan of at least one of the emitter/detector arrangements over just one half rotation.

12. The method as claimed in claim 1, wherein the at least one second recording is created from detector data of a scan of at least one of the emitter/detector arrangements over just one full rotation.

13. The method as claimed in claim 11, wherein a third recording is created from detector data of a scan of at least one of the emitter/detector arrangements over at least one full rotation and its image data is also subjected to a further filtering in respect of a third spatial frequency range and also included when creating the resulting recordings.

14. The method as claimed in claim 1, wherein the method is applied to the creation of cardiac recordings of a patient with a beating heart.

15. The method as claimed in claim 14, wherein the detector data originates from the temporal range of a cardiac cycle.

16. The method as claimed in claim 14, wherein the detector data originates from the temporal range of the rest phase of a cardiac cycle.

17. The method as claimed in claim 14, wherein the temporal focus of the detector data of the first recording is identical to the temporal focus of the detector data of the at least one second recording.

18. The method as claimed in claim 14, wherein the temporal focus of the detector data of the first recording is displaced in relation to the temporal focus of the detector data of the at least one second recording such that the data of the first recording is optimized in respect of its motion blur and moved into the temporal range of the detector data of the at least one second recording.

19. The method as claimed in claim 1, wherein tomographic sectional images are used as the recordings.

20. The method as claimed in claim 1, wherein 3D image data records are used as the recordings.

21. An x-ray CT system, comprising a control and computation unit including a program storage unit, computer program code being stored in the program storage unit and to execute the method of claim 1 during operation of the system.

22. The method as claimed in claim 2, wherein the filters used for high-pass and low-pass filtering are complementary in total.

23. The method as claimed in claim 3, wherein the filters used for high-pass and low-pass filtering are complementary in total.

24. The method as claimed in claim 4, wherein the filters used for high-pass and low-pass filtering are complementary in total.

25. The method as claimed in claim 2, wherein the filters used for high-pass and low-pass filtering are isotropic.

26. The method as claimed in claim 3, wherein the filters used for high-pass and low-pass filtering are isotropic.

27. The method as claimed in claim 4, wherein the filters used for high-pass and low-pass filtering are isotropic.

28. The method as claimed in claim 15, wherein the detector data originates from the temporal range of the rest phase of a cardiac cycle.

29. The method as claimed in claim 15, wherein the temporal focus of the detector data of the first recording is identical to the temporal focus of the detector data of the at least one second recording.

30. The method as claimed in claim 15, wherein the temporal focus of the detector data of the first recording is displaced in relation to the temporal focus of the detector data of the at least one second recording such that the data of the first recording is optimized in respect of its motion blur and moved into the temporal range of the detector data of the at least one second recording.

31. A computer readable storage medium including program segments for, when executed on a computer device, causing the computer device to implement the method of claim 1.

32. A system for creating tomographic recordings with the aid of an x-ray CT systems, which uses two emitter/detector arrangements operating with an angular offset on a gantry to scan an examination object simultaneously with at least two different x-ray energy spectra in a spiral or circular manner, the system comprising:
    means for reconstructing a first recording from combined detector data of a scan of a first of the two emitter/detector arrangements over a quarter rotation with a first x-ray energy spectrum and detector data of a scan of a second of the two emitter/detector arrangement over a complementary quarter rotation with a second x-ray energy spectrum;
    means for creating at least one second recording from detector data of a scan of at least one of the two emitter/detector arrangements over at least a half rotation;
    means for subjecting the first recording to high-pass filtering in respect of its spatial frequencies and subjecting the at least one second recording to low-pass filtering in respect of its spatial frequencies; and
    means for combining the filtered first and at least one second recording to produce a resulting recording.

* * * * *